United States Patent [19]

De Baets et al.

[11] Patent Number: 4,469,398

[45] Date of Patent: Sep. 4, 1984

[54] OPTICAL CONNECTOR FOR USE DURING PHOTOMETRIC ANALYSIS

[75] Inventors: Micheal C. De Baets, Santa Clara; John M. Sperinde, San Jose, both of Calif.

[73] Assignee: Oximetrix, Inc., Mountain View, Calif.

[21] Appl. No.: 315,427

[22] Filed: Oct. 27, 1981

[51] Int. Cl.³ .............................................. G02B 7/26
[52] U.S. Cl. .............................. 350/96.20; 350/96.10; 350/96.27; 356/39
[58] Field of Search ............. 350/96.10, 96.20, 96.23, 350/96.24, 96.27; 250/227; 356/39, 40, 41, 42

[56] References Cited

U.S. PATENT DOCUMENTS

| | | | |
|---|---|---|---|
| 3,441,352 | 4/1969 | Hughes | 356/39 X |
| 3,847,483 | 11/1974 | Shaw et al. | 356/41 |
| 4,003,707 | 1/1977 | Lübbers et al. | 356/39 X |
| 4,041,932 | 8/1977 | Fostick | 356/39 X |
| 4,166,961 | 9/1979 | Dam et al. | 356/39 X |
| 4,240,090 | 12/1980 | Hughes et al. | 350/96.27 X |
| 4,295,470 | 10/1981 | Shaw et al. | 356/41 X |
| 4,322,164 | 3/1982 | Shaw et al. | 356/41 X |

*Primary Examiner*—John D. Lee
*Attorney, Agent, or Firm*—Robert S. Kelly

[57] ABSTRACT

An optical connector for connecting photometric analysis equipment which includes a transmitting and receiving light pipe to a material such as flowing blood wherein the blood is not contaminated by the light pipe. The connector has a flow passage therethrough for connection to the blood flow conduit and a light pipe receiving passage extending at a right angle thereto. At the intersection of the passages there is provided an image transferring window, and the light pipe is arranged to be snugly received in the pipe receiving passage in abutment with the window. The image transferring properties of the window are such that no optical distortion occurs as light is transmitted from one face to the opposite face thereof. This is accomplished by forming the window of a coherent bundle of optical fibers of very small individual diameters in the order of 0.003 inches or less.

15 Claims, 11 Drawing Figures

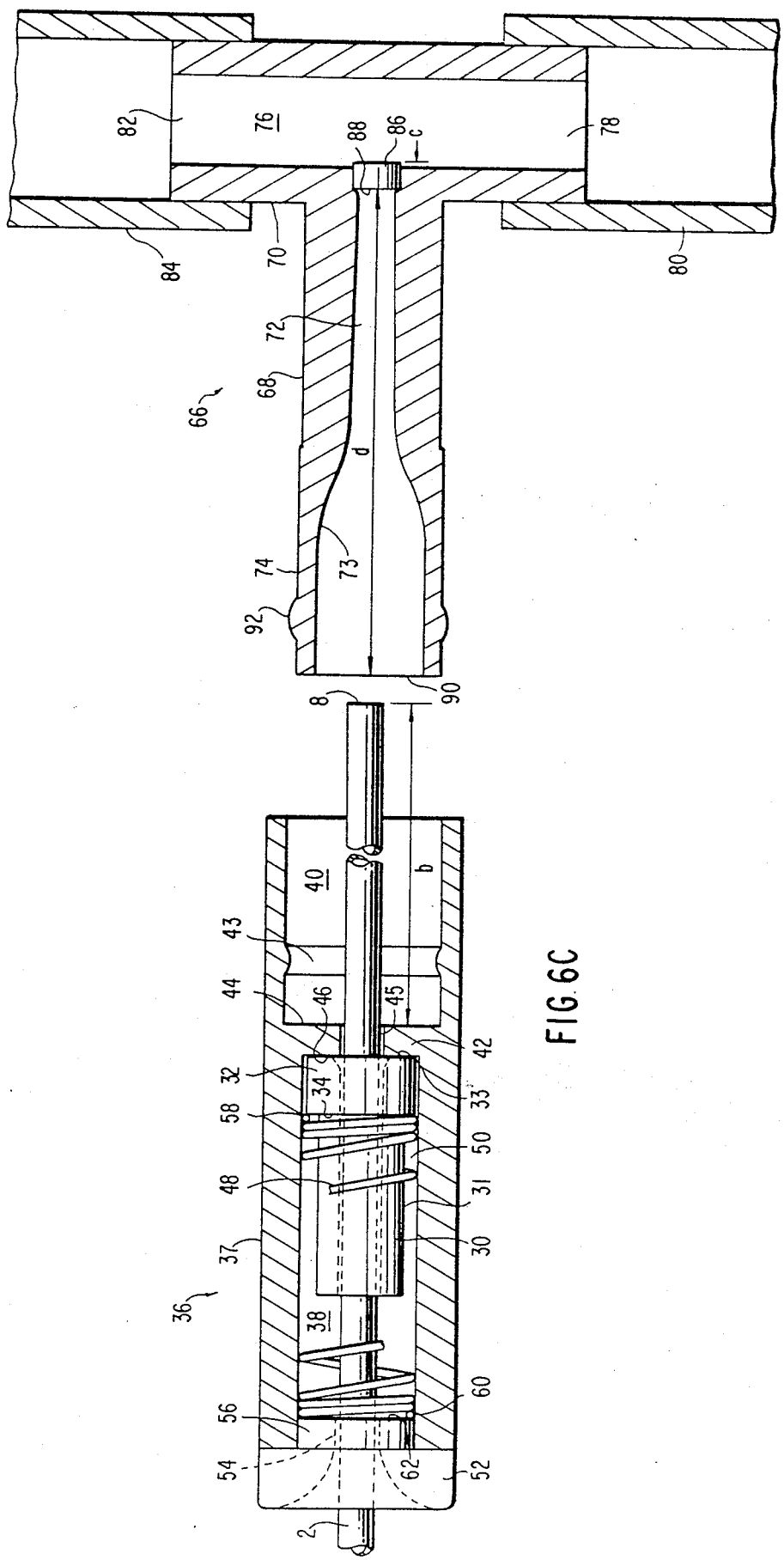

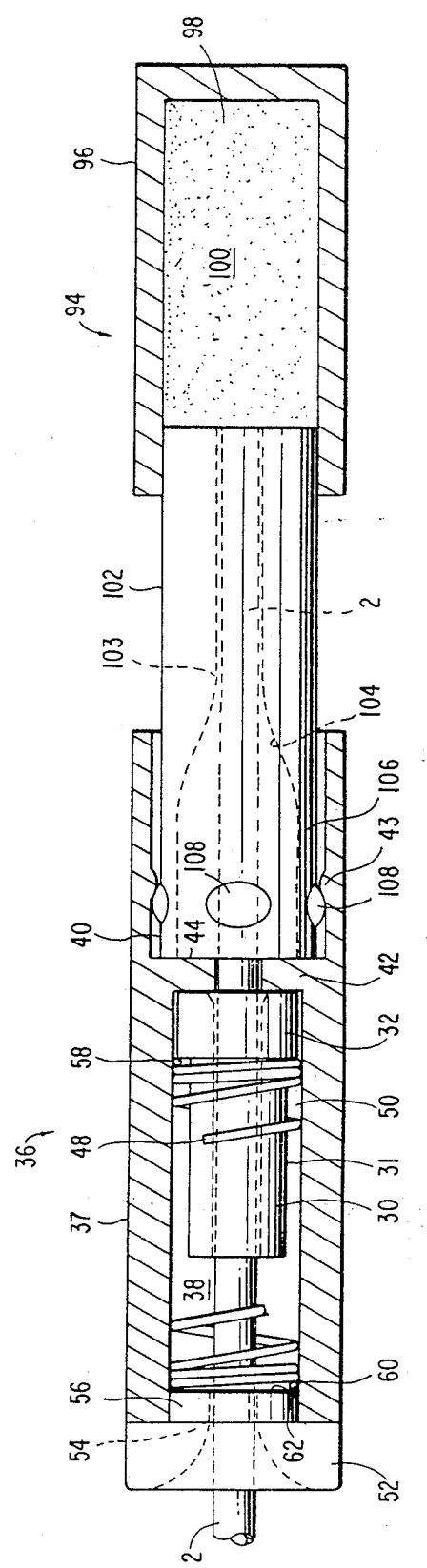

OPTICAL CONNECTOR FOR USE DURING PHOTOMETRIC ANALYSIS

TECHNICAL FIELD

The present invention relates to devices for optically connecting photometric analysis equipment to samples of fluid and more particularly relates to apparatus for connecting photometric analysis equipment having receiving and transmitting light pipes to flowing blood in a manner whereby the blood will not be contaminated by the photometric analysis equipment.

BACKGROUND ART

Optical geometry is a critical parameter in carrying out photometric analysis of various substances. For example, where a population of optical catheters are interchangeably used for transmitting light to and receiving reflected light from blood during measurements of oxyhemoglobin saturation ($SO_2$) levels, the establishment of uniform geometry between the optical apertures of the transmitting and receiving fibers in each member of the optical catheter population permits a universal calibration to be performed for the entire population of optical catheters. A means for achieving such uniform optical geometry from catheter to catheter is disclosed in co-pending application Ser. No. 964,612, filed Nov. 29, 1978 now U.S. Pat. No. 4,295,470, issued Oct. 20, 1981 and assigned to the assignee of the present invention. Once an initial calibration is performed with one of the members of the optical catheter population constructed in accordance with Ser. No. 964,612, any of the members of the catheter population can be utilized to measure oxyhemoglobin saturation by simply standardizing the light transmissive properties of the selected optical catheter. The tip of the selected optical catheter is thereafter inserted into the blood flow of a patient and the remaining end of the catheter is connected to an oximeter of the type disclosed in U.S. Pat. No. 3,638,640 issued Feb. 1, 1972 to Shaw; U.S. Pat. No. 3,847,483 issued Nov. 12, 1974 to Shaw et al, or U.S. Pat. No. 4,114,604 issued Sept. 19, 1978 to Shaw et al.

Where the population of optical catheters are designed for in vivo insertion, suitable surgical procedures are employed to place one selected member of the optical catheter population in the blood stream of a patient. Thereafter, any remaining member of the population of optical catheters can be used interchangeably with the first selected member as previously indicated. Where extracorporeal determinations of oxyhemoglobin saturation levels are required, such as may occur during cardiopulmonary bypass (CPB) operations, conventional optical catheter techniques are less efficient. Extracorporeal in vitro measurements of $SO_2$ can, of course, be obtained by inserting the tip of a selected optical catheter through appropriate tubing adaptors into the blood flowing through the cardiopulmonary bypass system. As is the case when in vivo measurements are involved, sterility, non-toxicity and cleaning considerations demand that catheters employed for in vitro measurements be disposed of after a single use. In contrast to the relatively long-term placement of optical catheters during in vivo $SO_2$ level monitoring, however, this short-time once only use of optical catheters to obtain extracorporeal, in vitro $SO_2$ measurements can prove unjustifiably expensive. Accordingly, a reliable and economically practical means for providing an external optical connection between photometric analyzing equipment and an extracorporeal sample of fluid would be of obvious advantage.

SUMMARY OF THE INVENTION

With the apparatus of the present invention a means is provided for readily obtaining a photometric analysis of extrasorporeal blood with conventional photometric analysis equipment including a catheter normally intended for insertion into the bloodstream of a patient. Thus, the apparatus includes a tubular member having a flow passage therethrough with the ends of the member being adapted to be connected to the conduit carrying the blood while it is out of the patient's body. The tubular member has a stem attached thereto and extending at an angle therefrom which stem has a relatively narrow interior passage that intersects the flow passage. The narrow stem passage serves to receive the end of the light transmitting and receiving member in close fitting relationship. A window is positioned at the intersection of the passages with one face exposed to the blood flow in the flow passage and the opposite face exposed to the end of the light transmitting and receiving member, thus insulating the member from the blood to prevent contamination. Since it is critical that the optical geometry of the transmitting and receiving light pipes remain unaltered with respect to the geometry which is present when the pipes are immersed in the blood flow, the window comprises an image transferring device so that the light pattern received on one face is transmitted to the other face and vice versa without optical distortion. Preferably, this device is made up of a bundle of coherent optical fibers extending between the faces and having very small individual diameters in the order of 0.003 inches or less.

It will thus be seen that the optical connector of the present invention permits a conventional catheter type input to photometric analysis equipment to be repeatedly used in making photomertric analysis of blood without contaminating the blood and without requiring any recalibrations due to optical distortion introduced by the connector.

BRIEF DECRIPTION OF THE DRAWINGS

Figure 3:
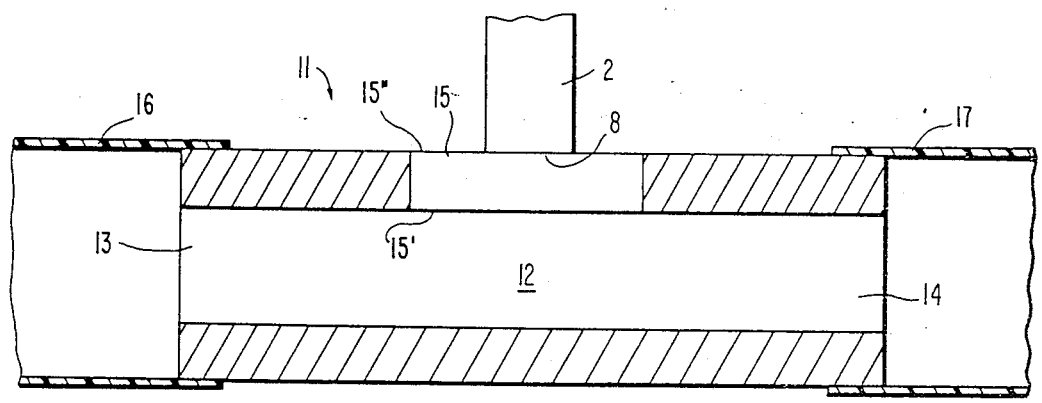
Figure 4:
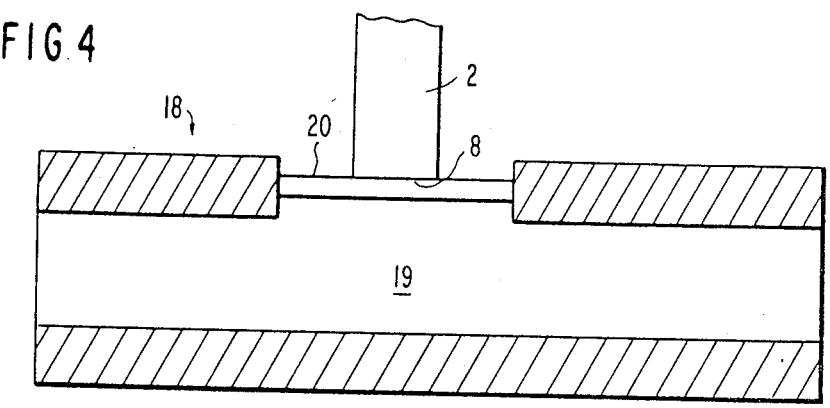
Figure 5:
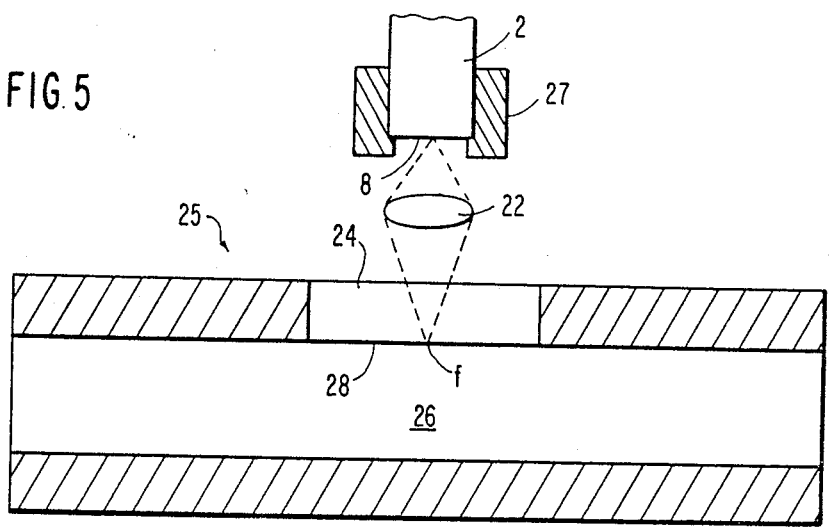

FIG. 3 schematically illustrates an optical connector constructed in accordance with the present invention, which optical connector employs an optical window comprising a bundle of individual optical fibers;

FIG. 4 is a schematic illustration of another embodiment of an optical connector which employs an optical window comprising a thin transparent substance;

FIG. 5 is yet another embodiment of an optical connector including a lens element for focusing radiant energy between the tip of the optical connector light guide and the optical window in the optical interfacing structure;

FIGS. 6A–6D illustrate the optical connector configuration of FIG. 3 in detail and the apparatus which is used to connect it to the photometric analysis equipment; and FIG. 7 illustrates a reference sheath which provides a reference standard for the optical connector of FIGS. 6A-6D.

BEST MODE FOR CARRYING OUT THE INVENTION

Figure 1:
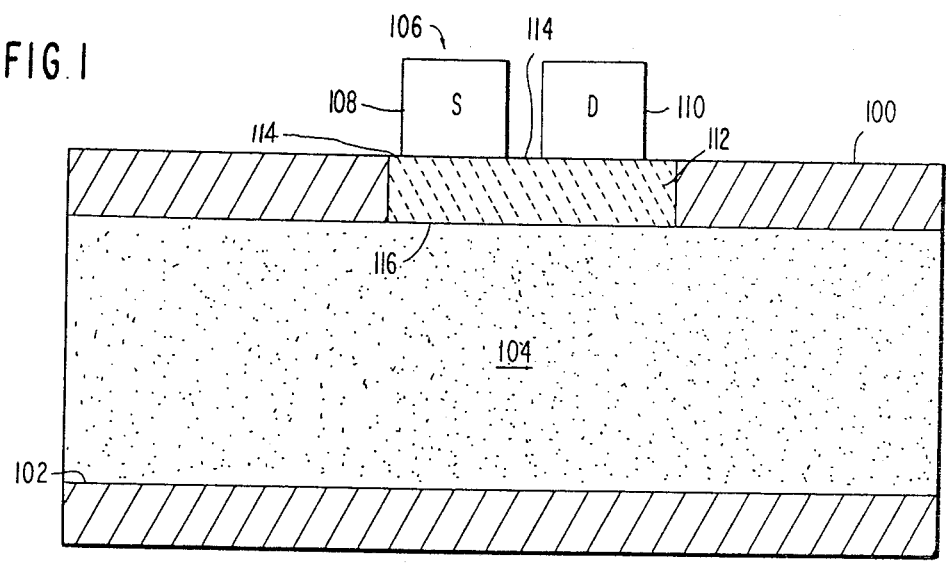
FIG. 1 is a schematic illustration of an optical connector having a chamber for holding a sample of material to be photometrically analyzed and an optical window means for passing radiant energy between the chamber and the exterior of the optical connector.

As previously indicated, the optical connector of the present invention is designed to optically interface a sample of material, particularly flowing blood, with photometric analysis equipment for the purpose of performing photometric analysis. The optical connector schematically illustrated in FIG. 1 thus comprises an optical interfacing structure 100 having a chamber 102 formed therein to receive the sample of material 104 being analyzed by photometric analysis equipment 106. During photometric analysis, radiant energy is directed toward the sample of material and at least partially reflected therefrom in a manner which provides an indication of the properties of the material. To this end, photometric analysis equipment 106 includes a source 108 of radiant energy and a radiant energy detector 110. Because changes in the geometry existing between the optical apertures of the radiant energy source and detector relative to the material undergoing analysis will affect the accuracy of the results of the analysis, direct or immediate physical contact between the optical apertures of the radiant energy source and detector and the sample of material should ideally be made. Such is the case, for example, where the sample of material is a fluid sample contained in a cuvette and the walls of the cuvette act as the optical apertures of the source and detector. Such is also the case where optical catheters are placed in the bloodstream of a patient during in vivo photometric analysis, bringing the optical apertures at the tip of the catheter directly into contact with the blood. If the photometric analysis is being conducted in vivo, however, the aforementioned considerations of sterility and non-toxicity render some sort of separation between the optical apertures of the source and detector and the sample of material highly advantageous. Accordingly, the optical interfacing structure 100 of the present invention is provided with an optical window means 112 through which radiant energy can pass. When the radiant energy source 108 and detector 110 are brought into abutment with the outer surface 114 of optical window means 112, optical communication with the sample of material 104 received in chamber 102 of optical interfacing structure 100 is achieved but physical contact between the sample and the source and detector is prevented.

The accuracy of the photometric analysis subsequently performed is enhanced by designing optical window means 112 to optically replicate or simulate the radiant energy-sample interface which would occur if the source and detector were in fact in direct physical contact with the sample. That is, optical window means 112 is designed to transfer images between the sample-window interface at the inner surface 116 of optical window means 112 and the outer surface 114 thereof with minimal distortion. Upon reaching the outer surface 114, radiant energy leaving source 108 appears to immediately enter the sample of material 104 in chamber 102, whereas radiant energy reflected from the sample of material appears immediately to enter detector 110 upon reaching inner surface 116. In this manner, the optical relationships which would exist if the optical apertures of the source and detector were actually immersed in the sample of material are reproduced to increase the accuracy of the photometric analysis while sterile and nontoxic conditions are maintained by the presence of optical window means 112 between the sample of material and the photometric analysis equipment. One type of optical window means suitable for accomplishing the desired image transfer is the image conduit available from American Optical Company, which image conduit consists of a coherent bundle of optical fibers having individual diameters of 0.003 inches or less.

The ability to optically transfer minimally-distorted images from the interior of optical interfacing structure 100 to the optical interfacing structure exterior enables the construction of a population of optical interfacing structures having uniform optical geometries. As long as the optical properties of the optical window means employed in each optical interfacing structure of the population are kept constant throughout the population, and as long as the optical apertures of the radiant energy source 108 and the detector 110 are brought into abutment with the outer surfaces of the optical window means, a uniform geometry between the optical apertures of the source and detector and the samples of material held in the chambers 102 of the optical interfacing structures can be maintained throughout the population of optical interfacing structures. Hence, even though periodic re-standardization of the photometric analysis equipment 106 may be necessary, the various members of the population of optical interfacing structures can be used interchangeably with one another for holding samples of material during photometric analysis without having to perform relatively long and complicated recalibrations of the photometric analysis equipment following each substitution of one optical interfacing structure for another.

Although optimum results are obtained by positioning the radiant energy source 108 and detector 110 of photometric analysis equipment 106 in abutting contact with the optical window means 112 of optical interfacing structure 100, it is often impractical to utilize photometric analysis equipment in this configuration during actual photometric analysis. If large numbers of photometric analysis measurements are required, for example, such as may occur in a hospital setting where a number of patients are simultaneously connected to cardiopulmonary by-pass systems, the photometric analysis equipment must be portable and the various optical components involved must have a quick connect/disconnect capability. Consequently, an intermediate optical communicator, e.g., a light pipe, is provided which can be affixed at one end to the portable photometric analysis equipment and quickly attached at the other end to a waiting optical interfacing structure.

Figure 2A:
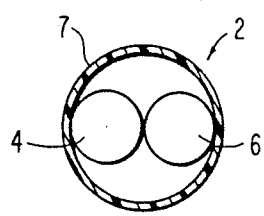
FIG. 2A is a cross-sectional view taken on line 1A—1A of FIG. 2B of a light pipe suitable for use with the optical connector of the present invention.
Figure 2B:
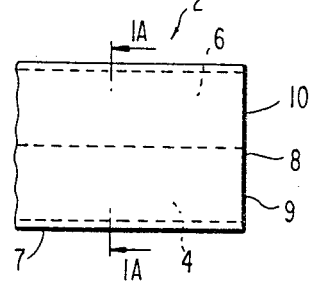
FIG. 2B is a top view of the light pipe of FIG. 2A.

FIG. 2A is a cross-sectional view and FIG. 2B is a top view of one type of light pipe 2 suitable for use with the optical connector interfacing structure of the present invention which receives a sample of material for analysis. Light pipe 2 comprises an optical transmitting fiber 4 for transmitting radiant energy to the sample of material and an optical receiving fiber 6 for receiving radiant energy reflected from the sample. A protective sheath 7 surrounds the two optical fibers 4 and 6. Although only one optical transmitting fiber 4 and one optical receiving fiber 6 are illustrated in FIG. 2A, it is understood that light pipe 2 can function satisfactorily with any number of optical transmitting fibers and any number of optical receiving fibers. One end of light pipe 2 is adapted for attachment to photometric analysis equipment (not shown in FIGS. 2A and 2B). Representative examples of photometric analysis equipment are disclosed in the aforementioned U.S. Pat. Nos. 3,638,640; 3,847,483 and 4,114,604. The remaining tip or end 8 of light pipe 2 containing the respective distal ends 9, 10 of optical transmitting and receiving fibers 4, 6 is designed to optically interface with the sample of material being analyzed. If a population of light pipes 2 are utilized to interact with a plurality of optical connectors as described below, it is necessary that each member of the light pipe population be constructed in uniform fashion to provide a constant optical relationship between the optical transmitting and receiving fibers from light pipe to light pipe. If desired, the light pipes 2 utilized for operation with the optical connectors may be selected from a population of light pipes wherein each and every optical transmitting fiber and each and every optical receiving fiber associated with the individual members of the light pipe population are constructed and oriented in the manner taught by U.S. Pat. No. 4,295,470, the disclosure of which is incorporated herein by reference. Hence, where the population of light pipes consist of single optical transmitting fiber—signal optical receiving fiber light pipes such as light pipe 2, the positional relationship between the distal end 9 of optical transmitting fiber 4 and the distal end 10 of optical receiving fiber 6 for each light pipe, as well as the respective shapes and cross-sectional areas of the distal ends 9, 10 are fixed and constant throughout the light pipe population. This positional relationship may be a co-planar relationship as illustrated in FIG. 2B, or it may be some other relative orientation capable of reproduction.

FIG. 3 illustrates in schematic form an optical connector configuration capable of providing a predetermined optical geometry at the light pipe-to-sample optical interference, whereby the predetermined optical geometry will remain uniform throughout a plurality of optical connectors constructed in accordance with the present invention. The optical connector configuration of FIG. 3 is specifically designed for use with fluid samples, and consequently employs an optical interfacing structure 11 including a chamber 12 having an inlet port 13 and an outlet port 14 for respectively receiving and discharging fluid to be analyzed. An optical window 15 is formed in one side of optical interfacing structure 11. Optical window 15 comprises an image conduit which, as indicated above in connection with FIG. 1, transfers images between the inner surface 15' of the optical window and the outer surface 15" thereof in order to replicate the optical relationships that would have existed between the distal ends 9, 10 of light pipe 2 and the fluid sample in chamber 12 had the light pipe 2 been inserted directly into the fluid. As also indicated above in connection with FIG. 1, the outer surface of optical window 15 provides an abutting contact surface (within manufacturing tolerances) for the tip 8 of light pipe 2. It can thus be seen that the optical window 15 fluidically isolates light pipe 2 from the fluid in chamber 12 while simultaneously permitting the transfer of images without distortion between the fluid and the distal ends 9, 10 (not shown in FIG. 3) of the optical transmitting and receiving fibers at the tip 8 of the light pipe. If the optical connector of FIG. 3 is used in connection with oxyhemoglobin saturation measurements during cardiopulmonary by-pass operations, inlet port 13 may be connected to a blood in-flow tube 16 while outlet port 14 is connected to a blood out-flow tube 17.

The abutting contact between the tip 8 of light pipe 2 and the optical window 15 in optical interfacing structure 11 serves two purposes. First, the abutting contact eliminates potential interference with the photometric analysis due to specular reflection from the surfaces of optical window 15. Second, and more importantly, the abutting contact establishes a fixed optical relationship between the distal ends 9, 10 of the optical transmitting and receiving fibers 4, 6 in light pipe 2 and the fluid in chamber 12 of the optical interfacing structure. During the manufacture of a population of optical interfacing structures 11, the optical properties of the optical windows 15 in the various individual optical interfacing structures are uniformly controlled such that constant image transfer characteristics are achieved. Consequently, whenever the tip 8 of a light pipe 2 selected from the population of light pipes disclosed in connection with FIGS. 2A and 2B is brought into abutting contact with an optical window 15 in any selected member of the population of optical interfacing structures 11, the original optical geometry existing between the distal ends of the optical transmitting and receiving fibers 4, 6 in light pipe 2 and the sample of fluid in chamber 12 is replicated. This ability to replicate optical geometries, i.e., to establish a uniform optical geometry at the light pipe-to-fluid optical interface for the entire population of light pipes relative to the entire population of optical interfacing members, makes possible the interchangeable use of members of the light pipe and optical interfacing structure populations without having to recalibrate the photometric analysis equipment each time a different light pipe and optical interfacing structure combination is involved.

Turning to FIG. 4, another configuration for an optical connector constructed in accordance with the present invention is schematically shown. The optical connector configuration of FIG. 4 exhibits the same optical geometry as the optical connector configuration of FIG. 3, and includes an optical interfacing structure 18 having a chamber 19 for holding the sample of fluid to be analyzed. The optical window 15 of FIG. 1, however, is replaced with a thin transparent window 20 having a thickness of 0.005 inches or less. The tip 8 of light pipe 2 is again brought into contact with thin transparent window 20 to establish a fixed optical relationship between the distal ends 9, 10 (not shown in FIG. 4) of the optical transmitting and receiving fibers 4, 6 in the light pipe and the fluid in chamber 19 of optical interfacing structure 18. In contrast to optical window 15, no special image transfer properties are associated with transparent window 20. Nevertheless, the thickness of transparent window 20 approaches zero thickness and effectively reduces distortion of radiant energy passing through the apertures of the optical transmitting and receiving fibers by minimizing the distance separating the fluid in chamber 19 from the distal ends of the optical transmitting and receiving fibers. As is the case with optical window 15, then, the light pipe-to-fluid interface that would exist if light pipe 2 were immersed in the fluid sample is optically replicated at the point of contact between transparent window 20 and the light pipe. It can also be seen that a population of optical interfacing structures having the configuration disclosed in FIG. 4 will all provide substantially uniform optical geometries with respect to the population of light pipes disclosed in FIGS. 2A and 2B, and again the various members of the light pipe and optical interfacing structure populations may be used interchangeably without having to recalibrate for each individual optical interfacing structure-light pipe combination.

FIG. 5 schematically depicts yet another optical connector configuration, wherein a lens element 22 is interposed between light pipe 2 and optical window 24 in optical interfacing structure 25. Optical interfacing structure 25, of course, includes a fluid-receiving chamber 26. Optical window 24 is a transparent type of window such as transparent window 20 of FIG. 4, although the thickness of optical window 24 may if desired be greater than the thickness of transparent window 20. Lens element 22 is positioned at a fixed distance from optical window 24. A stop means 27 also having a fixed position relative to optical window 24 is then used to hold light pipe 2 in a fixed position relative to both lens element 22 and optical window 24 such that radiant energy leaving the distal end 9 of optical transmitting fiber 4 (not shown in FIG. 5) in the tip 8 of light pipe 2 is focused on the fluid-optical window interface surface 28. Similarly, energy reflected back to the fluid-optical window interface surface 28 is focused by lens element 22 on the distal end 10 of optical receiving fiber 6 in the tip of the light pipe.

The ability to replicate the dimensions of the optical interfacing structure 25 in FIG. 5 for an entire population of optical interfacing structures permits the establishment of a uniform optical geometry between the distal ends of the optical transmitting and receiving fibers in light pipe 2 and the fluid in chamber 26. The members of the optical interfacing structure population may therefore be interchangeably employed with members of the light pipe population of FIGS. 2A–2B during photometric analysis of the fluid sample, using a uniform calibration obtained from the first such members so employed.

Figure 6A:
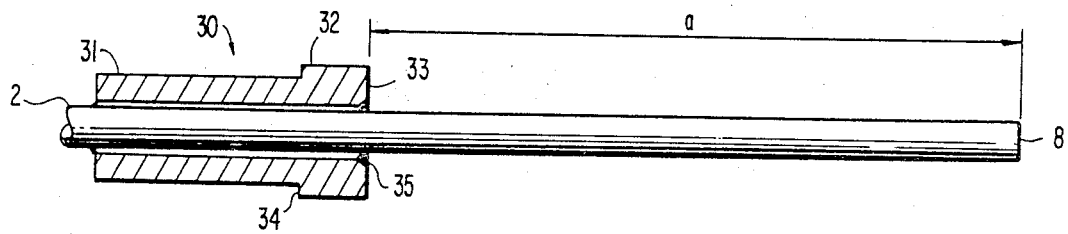
Figure 6B:
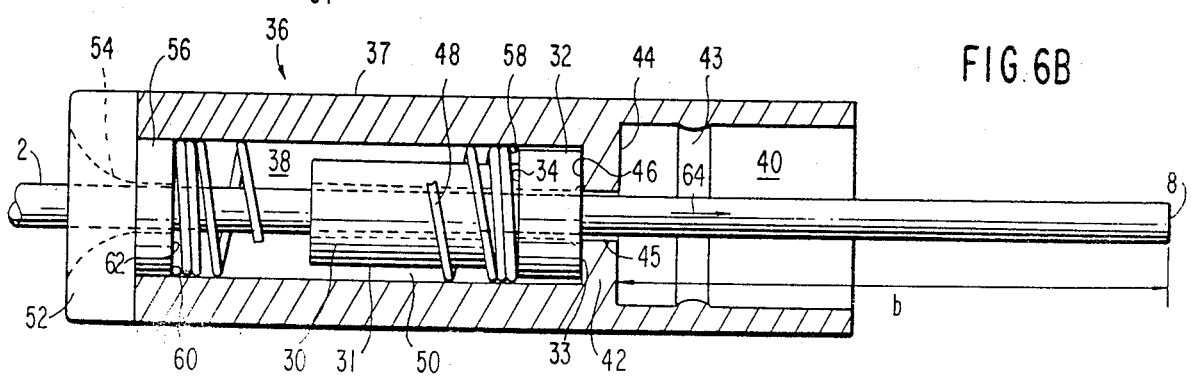

FIGS. 6A through 6D provide a detailed illustration of an optical connector such as that shown in FIG. 3. Turning first to FIG. 6A, it can be seen that a light pipe 2 selected from the population of light pipes disclosed in FIGS. 2A and 2B is inserted through a hollow plug 30 having an interior diameter slightly larger than the exterior diameter of the light pipe. Plug 30 is formed with a shank portion 31 at one end thereof and a flange portion 32 at the other end thereof. Flange portion 32 includes a front face 33 and a back face 34. A suitable adhesive 35 secures the plug to the light pipe such that the tip 8 of the light pipe is positioned at a predetermined distance a from the front face 33 of flange 32. Turning next to FIG. 6B, it can be seen that the plug and light pipe arrangement of FIG. 6A is inserted into the interior of an optical fitting structure 36 having a hollow body 37. Body 37, which may be fabricated from a durable material such as plastic or metal, contains two chambers 38 and 40 separated by an intervening wall 42. The diameter of chamber 38 corresponds roughly to the outer diameter of the flange portion 32 on plug 30. The diameter of chamber 40 may, if desired, be somewhat larger than the diameter of chamber 38. A rib 43 is formed around the periphery of chamber 40 proximate to the surface 44 of intervening wall 42. A cylindrical passage 45 in intervening wall 42 has a diameter slightly larger than the exterior diameter of light pipe 2, thus permitting the light pipe to pass from chamber 38 through chamber 40 until the surface 46 of intervening wall 42 contacts front surface 33 on the flange portion 32 of plug 30. At this point, the tip 8 of light pipe 2 is spaced a predetermined distance b from the surface 44 of intervening wall 42. A spring 48 is then mounted in chamber 38 around the shank portion 31 of plug 30 in the space 50 between the outer surface of the shank portion and the surface of chamber 38. Finally, a cap 52 having an interior passageway 54 formed therein is placed over light pipe 2 and bonded to body 37, sealing off chamber 38. Cap 52 has a shank section 56 shaped to fit snugly within chamber 38. One end 58 of spring 48 now rests against the back face 34 of flange portion 32, while the other end 60 of spring 48 rests against the front face 62 of shank section 56 on cap 52. The dimensions of spring 48 are chosen such that the insertion of shank section 56 in chamber 38 slightly loads the spring. The spring end 58 resting against the back face 34 of flange portion 32 consequently urges plug 30 and light pipe 2 in the direction of arrow 64.

FIG. 6C illustrates the manner of attaching the optical fitting structure 36 of FIGS. 6A and 6B to an optical interfacing structure 66. Optical interfacing structure 66 is of a type schematically shown in FIG. 3, although with suitable modification the optical fitting structure 36 could be used with the optical interfacing structures of FIGS. 4 and 5. The optical interfacing structure 66 includes a hollow stem section 68 adapted to engage optical fitting structure 36 and a hollow base section 70 adapted to receive a sample of fluid undergoing photometric analysis. Stem section 68 is formed with a chamber 72 which receives the light pipe 2 projecting from optical fitting structure 36. Chamber 72 may be flared, as indicated at 73, to assist in guiding light pipe 2 into the chamber. The upper portion 74 of stem section 68 has an outer diameter somewhat smaller than the diameter of chamber 40 in optical fitting structure 36. The base section 70 of optical interfacing structure 66 is formed with a hollow chamber 76 having an inlet port 78 connected to an in-flow tube 80 and an outlet port 82 connected to an out-flow tube 84. Inlet tube 80 supplies a sample of fluid to chamber 76 in preparation for performing a photometric analysis of the fluid. The fluid sample is removed from chamber 76 via out-flow tube 84. Where the optical connector of the present invention is employed for $SO_2$ monitoring during cardiopulmonary bypass operations, inflow and out-flow tubes 80 and 84 may be part of the CPB bypass system. The longitudinal axes of chambers 72 and 76 are preferably disposed at right angles to one another, although other angular orientations may also be utilized.

Figure 6D:
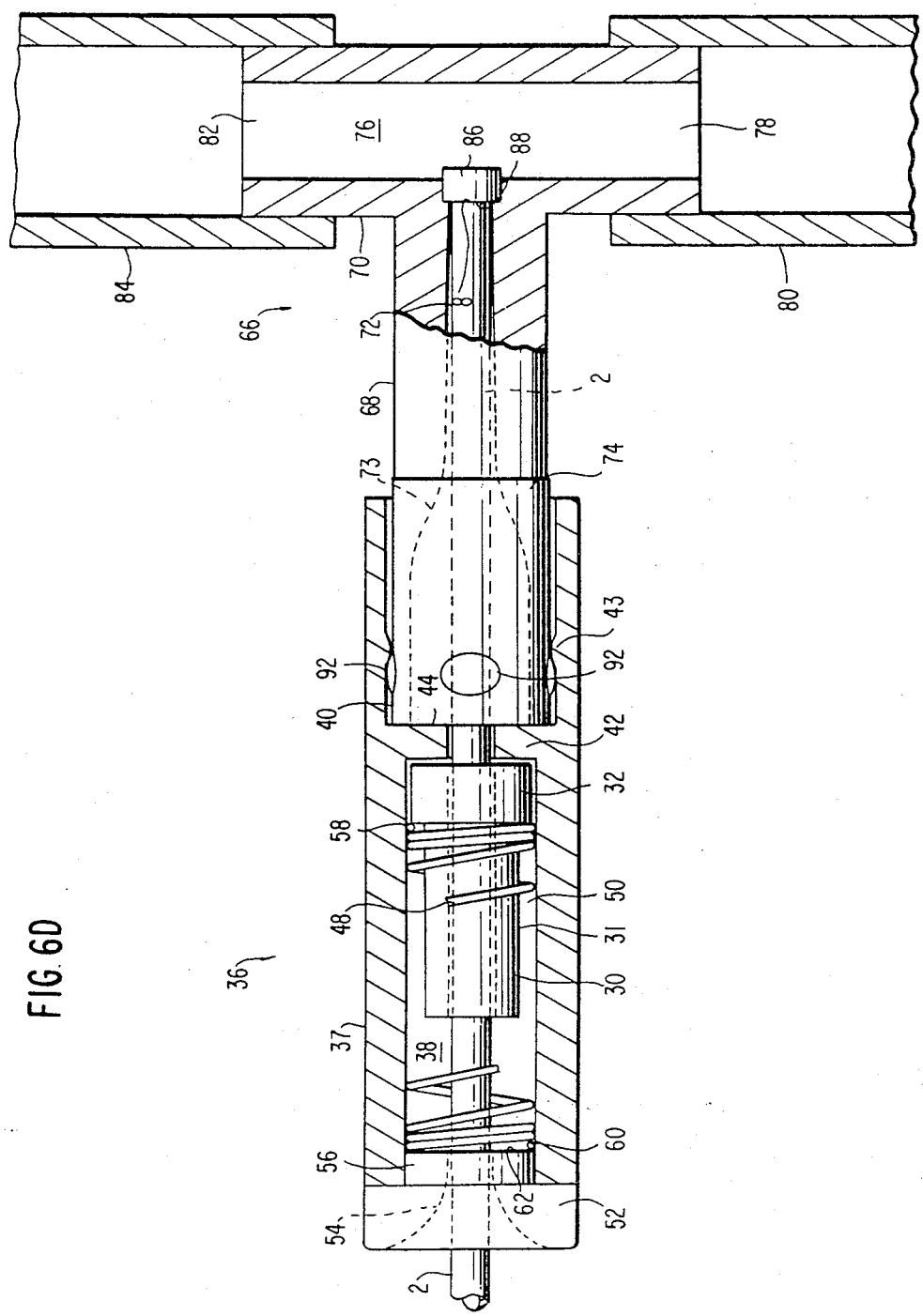

An optical window 86 having image transfer properties identical to those of optical window 15 in FIG. 3 separates chamber 72 in stem section 68 from chamber 76 in base section 70, fluidically isolating the two chambers while permitting optical communication therebetween. The optical window may project for a short distance c into chamber 76 if desired, while the inner surface 88 of the optical window is spaced at a predetermined distance d from the end 90 of stem section 68. In the preferred embodiment, this distance d is less than the distance b at which tip 8 of light pipe 2 is spaced from the surface 44 in optical fitting structure 36. When the light pipe 2 projecting from optical fitting structure 36 is inserted into the chamber 72 of optical interfacing structure 66, chamber 40 in the optical fitting structure 36 receives the upper portion 74 of stem section 68. It can now be seen that the differences between the distances b and d result in contact between the tip 8 of light pipe 2 and inner surface 88 of optical window 86 before upper portion 74 is fully received in chamber 40. Continued movement of the optical fitting structure toward the optical interfacing structure 66 thus forces the plug 30 secured to light pipe 2 against the bias exerted by spring 48 in chamber 38, whereupon the spring is further loaded to urge the tip 8 of light pipe 2 firmly against inner surface 88 of optical window 86. A series of bosses 92 positioned on the upper portion 74 of stem section 68 slide over the rib 43 formed on the interior of chamber 40 to provide positive engagement between the optical fitting structure 36 and the optical interfacing structure 66 after the upper portion 74 of stem section 68 has been fully inserted into chamber 40, as depicted in FIG. 6D.

Where respective populations of optical fitting structures and optical interfacing structures are manufactured in accordance with the present invention, employing light pipes selected from a population of light pipes also manufactured in accordance with the present invention, the aforementioned distances b and d as well as the spring constant of spring 48 are carefully controlled to provide a uniform force for urging the light pipe associated with each and every optical fitting structure against the optical window of each and every optical interfacing member. In this manner, it is possible to assure a uniform optical geometry between the optical apertures of the light pipe associated with each optical fitting structure in a first population of optical fitting structures and the sample of fluid received by each optical interfacing structure in a second population of optical interfacing structures. Such uniform optical geometry in turn permits the various members of the two populations to be used interchangeably without having to recalibrate the photometric analysis equipment every time one member of one of the populations is substituted for another member of that population. For example, if a light pipe associated with a given member of a population of optical fitting structures has already been connected to photometric analysis equipment and calibrated, that given member of the optical fitting structure population can be moved from one member of the optical interfacing structure population to another without recalibrating. Thus, in a hospital setting, a single light pipe/optical fitting structure connected to an oximeter and calibrated at the beginning of an oximeter monitoring period could be employed with the initial calibration serving as a universal calibration to obtain oxygen saturation measurements for any of a number of patients respectively connected to cardiopulmonary by-pass tubing networks, which networks include optical interfacing structures. In analogous fashion, a given member of an optical interfacing structure population can respectively receive the light pipes associated with various members of the optical fitting structure population and subsequent photometric analysis can be carried out using a universal calibration for each light pipe and optical fitting structure so received. Of course, the light transmissive properties unique to each light pipe will necessitate restandardization of the photometric analysis equipment each time a different light pipe is attached to the equipment. Nevertheless, by rendering the cumbersome recalibration process unnecessary, the optical fitting structure populations and optical interfacing structure populations of the present invention can provide a convenient means for performing a series of measurements during photometric analysis in a minimal amount of time.

A reference sheath 94 for performing oximeter standardization using the light pipe and optical fitting structure of FIGS. 6A-6D is shown in FIG. 7. The reference sheath 94 includes a holder 96 having a cavity 98 filled with an optical standard 100. Optical standard 100 comprises a material having constant reflectance properties as a function of incident radiation wavelength. Light directed toward optical standard 100 by a radiant energy source is reflected back from the optical standard in a manner such that predetermined ratios between the various wavelength components of the reflected light exist. Although any material of known reflectivity can be employed in the present invention, in the preferred embodiment optical standard 100 comprises a solid silicon material uniformly interspersed with a plurality of scattering particles such as disclosed in application Ser. No. 52,065, filed June 25, 1979 and assigned to the assignee of the present invention now U.S. Pat. No. 4,322,164, issued Mar. 30, 1982. An adaptor 102 projecting from holder 96 is bonded to the surface of cavity 98 in abutting relationship to optical standard 100. An interior passageway 103 in adaptor 102 has a diameter large enough to receive the light pipe 2 which projects from optical fitting structure 36. If desired, a flared surface 104 may be formed in passageway 103 at the upper portion 106 of adaptor 102 to assist in guiding light pipe 2 through the adaptor. The outer diameter of the adaptor is slightly smaller than the inner diameter of chamber 40 in the body 37 of optical fitting structure 36. Hence, in a manner similar to that utilized for connecting optical fitting structure 36 to optical interfacing structure 66, adaptor 102 may be inserted into chamber 40 of the optical fitting structure 36 until the tip 8 of light pipe 2 is brought into contact with optical standard 100. A series of bosses 108 can be formed on the upper portion 106 of adaptor 102, which bosses slide over the rib 43 formed in chamber 40 to provide for positive engagement between optical fitting structure 36 and reference sheath 94. The tip 8 of light pipe 2 is thus firmly held against optical standard 100. The free end of light pipe 2 is connected to an oximeter and the standardization sequence is performed as disclosed in the aforementioned Ser. No. 52,065. When standardization is complete, reference sheath 94 is removed from optical fitting structure 36 and the light pipe with attached optical fitting structure is ready for connection to an optical interfacing structure 66 as disclosed in FIGS. 6C and 6D. Reference sheath 94 may be discarded, or may be retained for use during subsequent standardization sequences.

INDUSTRIAL APPLICABILITY

Optical fitting structures and optical interfacing structures of the present invention may be conveniently manufactured in large populations and assembled together with selected light pipes from a population of light pipes to provide a plurality of devices for optically connecting photometric analysis equipment to a sample of material undergoing analysis. The various members of the light pipe, optical fitting structure and optical interfacing structure populations so manufactured can then be used interchangeably with one another. Uniform geometries established at the optical interface between samples of material held by members of the optical interfacing structure population and the optical apertures of selected light pipes secured by members of the optical fitting structure population are maintained for all possible combinations of the three populations, thereby eliminating the necessity for photometric recalibration each time a member of one population is substituted for another member of that population. The light pipe, optical fitting structure and optical interfacing structure of the present invention thus have wide applicability in situations where a number of optical measurements must be accurately and rapidly performed.

The present invention has been set forth in the form of several preferred embodiments. It is nevertheless understood that modifications to the optical fitting structure and the optical interfacing structure disclosed herein may be made by those skilled in the art without departing from the spirit and scope of the present invention. Moreover, such modifications and variations are considered to be within the purview of the appended claims.

What is claimed is:

1. In a system for performing photometric analysis of materials, which system employs a selected one of a population of light pipes for transmitting radiant energy to and from a sample of the material being analyzed, each selected light pipe including at least one optical transmitting fiber and at least one optical receiving fiber respectively having distal ends positioned in predetermined optical relationship to one another, an optical connector for optically connecting the distal ends of the optical transmitting and receiving fibers to the sample of material, said optical connector comprising an optical interfacing structure having a first interfacing chamber means disposed therein for receiving the sample of material and a second interfacing chamber means disposed therein for receiving the selected light pipe, said optical interfacing structure also having an optical window means for physically separating said first interfacing chamber means from said second interfacing chamber means while conducting radiant energy therebetween, said optical connector also comprising an optical fitting structure which engages said optical interfacing structure and supports the selected light pipe within said second interfacing chamber means of said optical interfacing structure such that the distal ends of the optical transmitting and receiving fibers in the selected light pipe are held in fixed optical relationship to the sample of material received in said first interfacing chamber means.

2. The optical connector set forth in claim 1, wherein said optical fitting structure includes a biasing means for urging the selected light pipe into a position such that the distal ends of the optical transmitting and receiving fibers in the selected light pipe are held in said fixed optical relationship to the sample of material received in said first interfacing chamber means.

3. An optical connector as set forth in claim 2, wherein said optical fitting structure includes a plug structure secured to the selected light pipe, said optical fitting structure also including a hollow body structure having a passageway formed therein to receive the selected light pipe and a first fitting chamber formed therein to receive said plug structure when said passageway receives the selected light pipe.

4. An optical connector as set forth in claim 3, wherein said biasing means includes a spring mounted in said first fitting chamber to exert a force against said plug structure, said force serving to urge the selected light pipe into said position such that the distal ends of the optical transmitting and receiving fibers in the selected light pipe are held in said fixed relationship to the sample of material received in said first interfacing chamber means.

5. An optical connector as set forth in claim 3, wherein said optical interfacing structure includes a stem section having said second interfacing chamber means formed therein and said optical fitting structure includes a second fitting chamber at the remaining end of said passageway, said second fitting chamber having a diameter sufficient to receive said stem section of said optical interfacing structure when the selected light pipe is received by said second interfacing chamber means in said stem section.

6. An optical connector as set forth in claim 5, wherein said optical fitting structure includes an engaging means which positively engages said optical interfacing structure when the selected light pipe is received in said second interfacing chamber means of said optical interfacing structure.

7. An optical connector as set forth in claim 6, wherein said engaging means includes a rib structure formed around the periphery of said second fitting chamber in said optical fitting structure, said optical interfacing structure including projecting means formed at one end of said stem section for engaging said rib structure when said stem section is received by said second fitting chamber of said optical fitting structure.

8. An optical connector as set forth in claim 1, wherein the material being analyzed is a fluid and said first interfacing chamber means in said optical interfacing structure has a first opening connected to receive a flow of fluid to be analyzed and a second opening connected to discharge the flow of fluid so received.

9. An optical connector as set forth in claim 1, wherein said optical interfacing structure includes a lens element mounted in said second interfacing chamber means, said lens element being positioned between the distal ends of the optical transmitting and receiving fibers in the selected light pipe when the selected light pipe is received by said second interfacing chamber means.

10. An optical connector comprising a rigid tubular member having a flow passage extending therethrough and including end portions adapted to be connected to fluid conduits for transporting fluid such as blood into and out of said passage, said tubular member having a stem section extending at an angle to said flow passage, said stem section having a relatively narrow passage therein for receiving a light transmitting and receiving pipe in close fitting relationship, and a window positioned at the intersection of the flow passage and the passage in the stem section, said window having one face exposed to the fluid in said flow passage and the opposite face exposed at the bottom of the stem section passage for receiving the end of said pipe, and said window comprising an image transferring device with the light pattern received on said one face being transmitted to said opposite face and vice versa without optical distortion.

11. An optical connector according to claim 10 wherein said window comprises a coherent bundle of optical fibers extending from said one face to said opposite face.

12. An optical connector according to claim 11 wherein said fibers have individual diameters in the order of 0.003 inches or less.

13. An optical connector according to claim 10 wherein said stem section is cylindrical in shape and includes means on the exterior surface thereof for permitting the light transmitting and receiving pipe to be tightly secured within the passage in the stem section and in abutment with said window.

14. An optical connector according to claim 13 wherein said securing means comprises a raised portion on said exterior surface of the stem section adapted to be received in an internal groove on a cylindrical fitting structure carried by said light transmitting and receiving pipe.

15. An optical connector according to claim 10 wherein said stem section passage extends at generally a right angle to the flow passage.

* * * * *